United States Patent

Paust et al.

Patent Number: 6,103,940
Date of Patent: Aug. 15, 2000

[54] PREPARATION OF ZEAXANTHIN, INTERMEDIATES FOR THIS PREPARATION, AND THE PREPARATION THEREOF

[75] Inventors: Joachim Paust, Neuhofen; Wolfgang Kriegl, Ludwigshafen, both of Germany

[73] Assignee: BASF Aktiengesellschaft, Ludwigshafen, Germany

[21] Appl. No.: 09/090,230

[22] Filed: Jun. 4, 1998

[30] Foreign Application Priority Data

Jun. 4, 1997 [DE] Germany .................... 197 23 480

[51] Int. Cl.⁷ .................................................. C07C 35/18
[52] U.S. Cl. .................. 568/823; 568/9; 568/11; 549/459
[58] Field of Search .................. 549/459; 568/9, 568/11, 823

[56] References Cited

U.S. PATENT DOCUMENTS

| | | | |
|---|---|---|---|
| 2,521,113 | 9/1950 | Braconier et al. | 260/498 |
| 3,988,205 | 10/1976 | Boguth et al. | 195/51 R |
| 4,134,922 | 1/1979 | Leeder | 568/9 |
| 4,177,126 | 12/1979 | Doorakian et al. | 568/11 |
| 4,225,527 | 9/1980 | Bollag et al. | 568/11 |
| 5,504,230 | 4/1996 | John et al. | 568/9 |

FOREIGN PATENT DOCUMENTS

| | | |
|---|---|---|
| 0 100 839 | 2/1984 | European Pat. Off. . |
| 0 120 341 | 10/1984 | European Pat. Off. . |
| 0 131 130 | 1/1985 | European Pat. Off. . |
| 0 165 647 | 12/1985 | European Pat. Off. . |
| 0 283 979 | 9/1988 | European Pat. Off. . |
| 25 37 060 | 3/1976 | Germany . |
| 812267 | 4/1959 | United Kingdom . |
| 1173063 | 12/1969 | United Kingdom . |

OTHER PUBLICATIONS

CA 126:19071, 1996.
CA 122:133469, 1995.
CA 107:134225, 1987.
CA 106:156186, 1986.

(List continued on next page.)

*Primary Examiner*—Amelia Owens
*Attorney, Agent, or Firm*—Oblon, Spivak, McClelland, Maier & Neustadt, P.C.

[57] ABSTRACT

Preparing (3R, 3'R)-zeaxanthin of the formula I

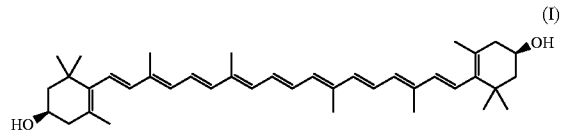

(I)

starting from (4-hydroxy-2,2,6-trimethylcyclohexanone of the formula II

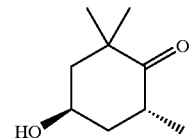

(II)

via the novel intermediates (4R,6R)-1-formyl-2,2,6-trimethyl-7-oxabicyclo[2.2.1]heptane of the formula IV

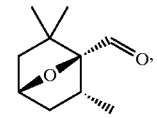

(IV)

(4R,6R)-1-(3-oxo-1-butenyl)-2,2,6-trimethyl-7-oxabicyclo[2.2.1]heptane of the formula V

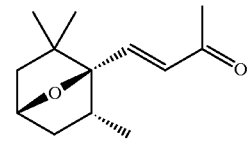

(V)

(4R,6R)-1-(3-hydroxy-3-methyl-1,4-pentadienyl)-2,2,6-trimethyl-7-oxabicyclo[2.2.1]heptane of the formula VI

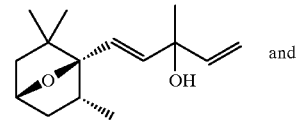

(VI)

and

[5-(4R,6R)-(4-hydroxy-2,2,6-trimethyl-1-cyclohexylidene)-3-methyl-1,3-pentadienyl]triarylphosphonium salt of the formula iso-III

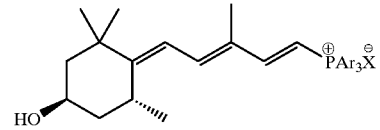

(iso-III)

where Ar is aryl and X is one equivalent of an anion of a strong acid. The (4R,6R)-1-formyl-2,2,6-trimethyl-7-oxabicyclo[2.2.1]heptane of formula IV is obtained by reacting the ketone of the formula II with dichloromethyllithium, which can be prepared by metallation of dichloromethane with butyllithium or lithium diisopropylamide.

13 Claims, No Drawings

OTHER PUBLICATIONS

August Ruettimann, et al., Helvetica Chemical Acta, vol. 63, pp. 1456–1462, "Synthese Von Optisch Aktiven, Natuerlichen Carotinoiden Und Strkturell Verwandten Naturproducten", 1980.

Hiroaki Taguchi, et al., Tetrahedron Letters, No. 27, pp. 2465–2468, "A New Synthesis of Alpha, Beta–Unsaturated Aldehydes Including (E)2–Methyl–2–Alkenal", 1973.

Widmer, et al. "Technical Procedures for the Syntheses of Carotenoids and Related Compounds from 6–Oxo–isophorone: Syntheses of (3R,3'R)–Zeaxathin,", Helvetica Chimica Acta, vol. 73, (1990), pp. 861–867.

Soukup, et al. "Technical Procedures for the Syntheses of Carotenoids and Related Compounds from 6–Oxo–isophorone: Syntheses of (3R,3'R)–Zeaxanthin Part II", Helv. Chimica Acta, vol. 73, (1990), pp. 868–873.

Taguchi, et al. "A New Synthesis of α,β–Unsaturated Aldehydes Including (E)2–Methyl–2–Alkenal", Tetrahedron Letters No. 27, (1973), pp. 2465–2468.

Ramsay, "Intensities and Shapes of Infrared Absorption Bands of Substances in the Liquid Phase", The Journal of the American Chemical Society, vol. 74, Jan.–Mar. (1952), pp. 72–80.

Oroshnik, et al. "Synthesis of Polyenes. I. Retrovitamin A Methyl Ether. Spectral Relationships between the β–Ionylidene and Retroionylidene Series, " The Journal of the American Chemical Society, vol. 295, Jan.–Mar. (1952) pp. 295–304.

Schlittler, et al, "Über die Alkaloide aus Strychnos melinoniana Baillon ", Helvetica Chimica Acta, vol. 35, (1952), pp. 29–45.

Schindler, et al. "Identifizierung von Substanz Nr. 763 aus Strophanthus speciosus und S. Boivinii als Strospesid (Desgluco–digitalinum–verum)", Helvetica Chimica Acta, vol. 35, No. 56 (1952), pp. 442–447.

Ishikawa, "The Synthesis of β–Ionylideneacetaldehyde" Bulletin of the Chemical Society of Japan, vol. 37, No. 2 (1964), pp. 207–209.

Torii, et al., "Electrooxidative Cleavage of Carbon—Carbon Linkages. 1. Preparation of Acyclic Oxoalkanoates from 2–Hydroxy– and 2–Acetoxy–1–cycloalkanones and Cycloalkanone Enol Acetates", The Journal of Organic Chemistry, vol. 47, No.1 (1982), pp. 47–52.

Rosenberger, et al., "Canthaxanthin. A New Total Synthesis", The Journal of Organic Chemistry, vol. 47, No. 11 (1982), pp. 2130–2134.

Rüttimann, et al., "Synthese von optisch aktiven, natürlichen Carotinoiden und strukturell verwandten Naturprodukten V. Synthese von (3R, 3'R)–, (3S, 3'S)–und (3R, 3'S; meso)–Zeaxanthin durch asymmetrische Hydroborierung. Ein neuer Zugang zu optisch aktiven Carotinoidbausteinen", Helvetica Chimica Acta, vol. 63, No. 154 (1980), pp. 1456–1462.

Chemical Abstracts, vol. 112, No. 7, Feb. 12, 1990, AN 54986a, DD 267,629, May 10, 1989.

Chemical Abstracts, vol. 112, No. 7, Feb. 12, 1990, AN 54987b, DD 265, 289, Mar. 1, 1989.

Chemical Abstracts, vol. 69, No. 26, Dec. 23, 1968, AN 108210g, U.S.S.R 220,957, Jul. 1, 1968.

Chemical Abstracts, vol. 119, No. 22, Nov. 29, 1993, AN 231586n, Hideki Nagata, et al., "Analytical Study of the Formation of Hemimorphite. I. Analysis of the Crystallization Process by the Co–Precipitation Method".

Chemical Abstracts, vol. 72, No. 6, Feb. 9, 1970, AN 27871h, A. G. Merkulov, et al., "Low–Temperature Synthesis of Zinc Silicates".

Chemical Abstracts, vol. 102, No. 24, Jun. 17, 1985, AN 206083n, JP 60–11219, Jan. 21, 1985.

PREPARATION OF ZEAXANTHIN, INTERMEDIATES FOR THIS PREPARATION, AND THE PREPARATION THEREOF

The invention relates to a novel synthetic route for preparing zeaxanthin, to processes for preparing intermediates in this novel zeaxanthin synthesis, and to novel intermediates in this process, in particular specific 7-oxabicyclo [2.2.1]heptane derivatives.

(3R,3'R)-Zeaxanthin (3,3'-dihydroxy-β,β-carotene) of the formula I

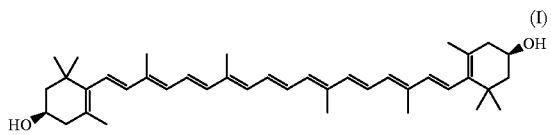

is a yellow pigment which is widespread in nature and occurs, inter alia, in corn, in egg yolk and in human and animal adipose tissue. It was isolated in crystalline form for the first time in 1929 from corn, and was subsequently identified as 3,3'-dihydroxy-β,β-carotene. It was shown, by correlation with fucoxanthin, that zeaxanthin has the (3R, 3'R) configuration. Optically inactive zeaxanthin was prepared some time ago by various synthetic routes (cf. GB 812, 267 and GB 1,173,063).

Because of the continually increasing demand for nature-identical dyes, there has been no lack of attempts to develop processes for the industrial preparation of (3R, 3'R)-zeaxanthin.

Accordingly, various routes for preparing zeaxanthin have been described in the literature. Reactions and intermediates which have proven suitable for this are the following:

1) The use of possibly enantiomerically pure 4-hydroxy-2,2,6-trimethylcyclohexanone (II) as building block for the cyclic end groups of zeaxanthin and 2) the preparation of zeaxanthin by Wittig reaction of two moles of a $C_{15}$-triphenylphosphonium salt of the formula III with the symmetric $C_{10}$-dialdehyde 2,7-dimethyl-2,4,6-octatrienedial (III)

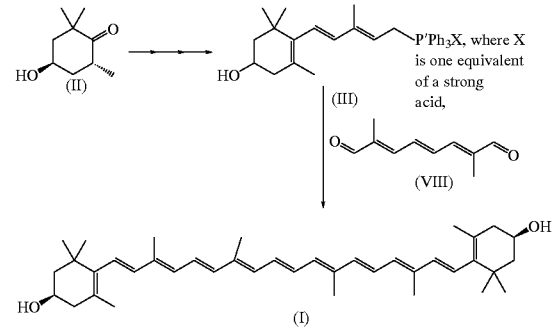

However, the various synthetic routes differ considerably in the way of obtaining the required $C_{15}$-triphenylphosphonium salt from the $C_9$ building block II.

There has been intensive work on the $C_9+C_6 \rightarrow C_{15}$ synthetic concept which is depicted diagrammatically hereinafter. For example, the $C_{15}$ intermediate obtainable by linking 4-hydroxy-2,2,6-trimethylcyclohexanone with a protected OH group (2; PG=protecting group) to the protected lithium $C_6$-acetylide 3 has been dehydrated by treatment with hydrochloric acid (cf. EP 100 839) or by ester elimination (cf. EP 131 130) to give the compound 4, the latter has been converted into the acetylenic phosphonium salt 5, and the $C_{15}$-triphenylphosphonium salt of the formula III has been prepared therefrom by partial hydrogenation.

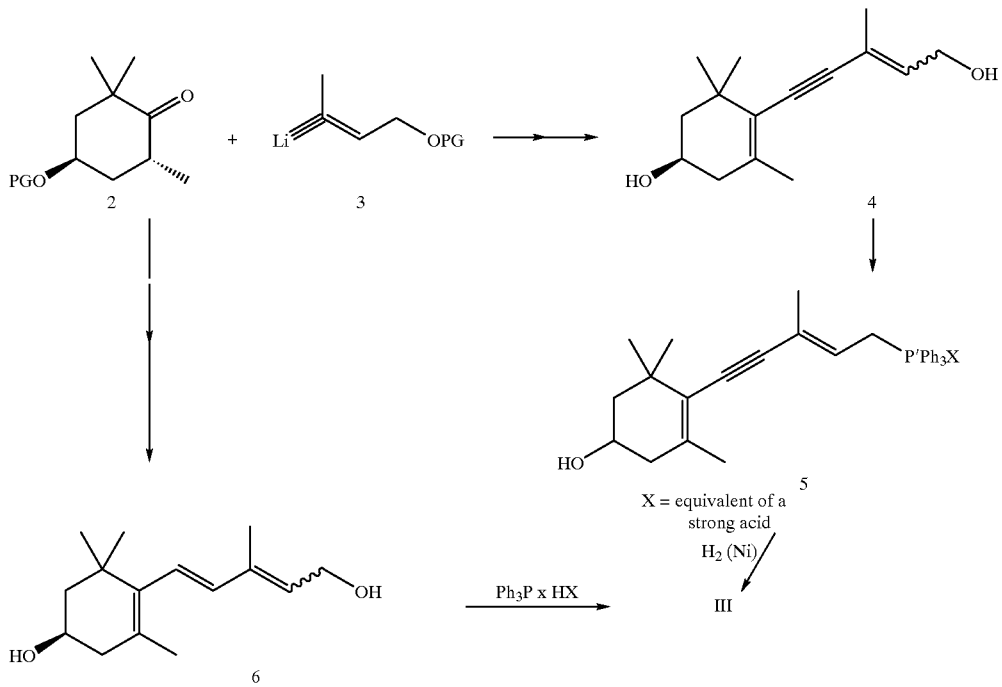

EP 120 341 describes direct reduction, with aluminum hydrides, of the $C_{15}$ intermediate obtainable by linkage of 2 and 3, dehydration of the resulting 3-methyl-2,4-pentadien-1-ol derivative under special conditions (cf. EP 454002), and conversion of the resulting 3-hydroxy-β-ionylideneethanol 6 into the triphenylphosphonium salt of the formula III.

The variants of this $C_9+C_6 \rightarrow C_{15}$ synthetic concept have been evaluated in Helv. Chim. Acta 73 (1990) 861. The authors conclude that economic preparation of zeaxanthin is not possible by these routes, because the instability of individual stages and the formation of (9Z) isomers result in the overall yields of the triphenylphosphonium salt of the formula III being mediocre.

State of the art for the industrial preparation of zeaxanthin is the $C_9+C_2+C_4 \rightarrow C_{15}$ synthetic concept (cf. EP 283 979 and Helv. Chim. Acta 73 (1990) 868). This involves conversion of the $C_9$-hydroxy ketone II into the $C_{15}$-triphenylphosphonium salt of the formula III via the $C_{11}$-acetylenecarbinol 7 and the $C_{15}$-acetylenecarbinol 8, with an overall yield of 70%.

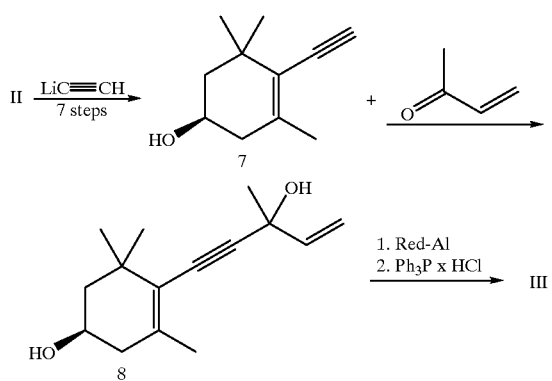

However, the synthesis of the $C_{15}$-triphenylphosphonium salt of the formula III via 7 and 8 is economically and ecologically unsatisfactory. This is because the reaction conditions required for the total of ten stages are vastly different. They cover the entire pH range and a temperature range from −20° C. to +130° C. and require changing solvents which differ greatly in polarity. The vast differences in the reaction conditions make great demands on the materials of the apparatus used, and also result in the need to introduce, and eliminate again and dispose of, protective groups on three occasions.

It is an object of the present invention to develop a novel process for the industrial preparation of zeaxanthin which avoids the prior art disadvantages described above, ie. to develop a process which can be used to obtain the required zeaxanthin in good yields starting from the readily available optically active (4R)-4-hydroxy-2,2,6-trimethylcyclohexanone of the formula II in a small number of reaction stages which can easily be implemented industrially.

It is another object of the invention to provide novel intermediates for the novel zeaxanthin process and to develop advantageous processes for the preparation thereof.

We have found that these objects can be achieved by the preparation of zeaxanthin in good yields starting from the readily available (4R)-4-hydroxy-2,2,6-trimethylcyclohexanone of the formula II in only 5 reaction steps which can be carried out relatively easily industrially via interesting novel intermediates and the isomeric, chemically equivalent $C_{15}$ triphenylphosphonium salts of the formula III and iso-III

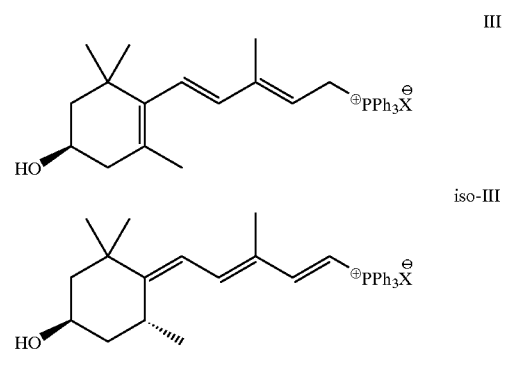

with the introduction and elimination again of protective groups being unnecessary.

The invention therefore relates to a process for preparing (3R, 3'R)-zeaxanthin of the formula I

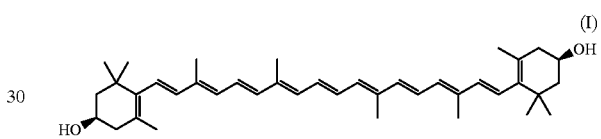

by the novel synthetic scheme of $C_9+C_1+C_3+C_2 \rightarrow C_{15}$; 2 $C_{15}+C_{10} \rightarrow C_{40}$, which comprises A. (4R)-4-hydroxy-2,2,6-trimethylcyclohexanone of the formula II

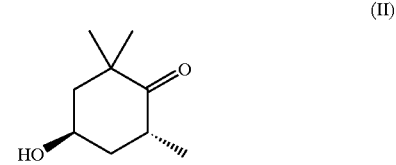

being reacted with dichloromethyllithium in an inert solvent at from −120 to −40° C., B. the novel (4R,6R)-1-formyl-2,2,6-trimethyl-7-oxabicyclo[2.2.1]heptane of the formula IV

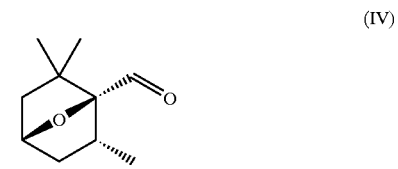

which is obtained on warming the reaction mixture to 20 to 60° C., being reacted either in isolated form or else directly in the form of the resulting reaction mixture with acetone or a dialkyl 2-oxopropylphosphonate, C. the resulting novel (4R,6R)-1-(3-oxo-1-butenyl)-2,2,6-trimethyl-7-oxabicyclo[2.2.1]heptane of the formula V

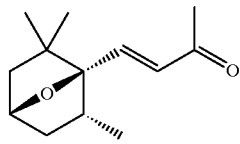
(V)

being converted in a conventional way by vinylation or ethynylation and subsequent partial hydrogenation into the novel (4R,6R)-1-(3-hydroxy-3-methyl-1,4-pentadienyl)-2,2,6-trimethyl-7-oxabicyclo[2.2.1]heptane of the formula VI

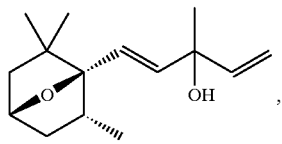
(VI)

D. the latter being reacted with a triarylphosphine, preferably triphenylphosphine, and a strong acid to give a mixture of the $C_{15}$-triarylphosphonium salt of the formula III and the novel isomer of the formula iso-III

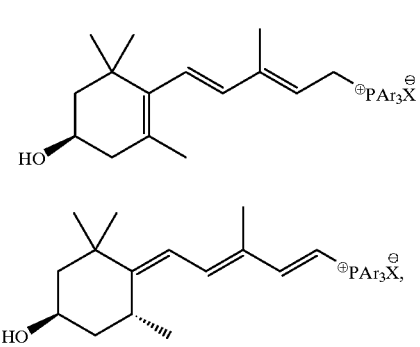
(III)

(iso-III)

where Ar is an aryl radical, preferably an unsubstituted or substituted phenyl radical, and X is one equivalent of an anion of a strong acid, in particular Cl, Br or $(HSO_4)$, and E. in each case the resulting mixture of the $C_{15}$-triarylphosphonium salt III and the novel iso-III being converted by a double Wittig reaction with 2,7-dimethyl-2,4,6-octatrienedial of the formula VIII

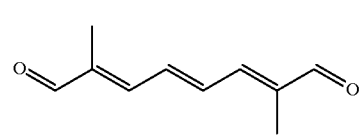
(VIII)

into zeaxanthin of the formula I.

The invention furthermore relates to the novel intermediate (4R,6R)-1-formyl-2,2,6-trimethyl-7-oxabicyclo[2.2.1]heptane of the formula IV

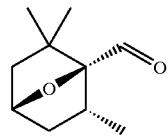
(IV)

and to a process for its preparation, which comprises (4R)-4-hydroxy-2,2,6-trimethylcylohexanone of the formula II (II)

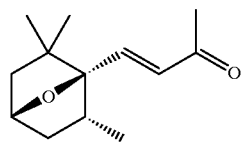

being reacted with the dichloromethyllithium, which is obtained by metallation of dichloromethane with alkyllithium compounds at from −120 to −70° C. or with lithium dialkylamides at from −70 to −40° C., in an inert solvent at from −120 to −40° C., the resulting reaction mixture being warmed, in the presence or absence of an alkali metal alcoholate or an alkali metal hydroxide, to from 20 to 60° C.

The invention additionally relates to the novel intermediate (4R,6R)-1-(3-oxo-1-butenyl)-2,2,6-trimethyl-7-oxabicyclo[2.2.1]heptane of the formula V

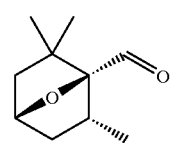
(V)

and to a process for its preparation, which comprises the novel (4R,6R)-1-formyl-2,2,6-trimethyl-7-oxabicyclo [2.2.1]heptane of the formula IV

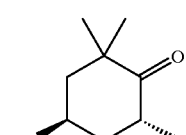
(IV)

being reacted either in isolated form or directly in the form of the reaction mixture obtained on reacting (4R)-4-hydroxy-2,2,6-trimethylcyclohexanone of the formula II (II)

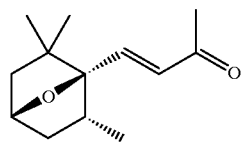

with dichloromethyllithium, which has been obtained by metallation of dichloromethane with alkyllithium compounds at from −120 to −70° C. or with lithium dialkylamides at from −70° C. to −40° C., in an inert solvent at from −120 to −40° C., and subsequently warming to 20 to 60° C., with acetone in an aldol condensation.

The invention furthermore relates to the novel intermediate (4R,6R)-1-(3-hydroxy-3-methyl-1,4-pentadienyl)-2,2,6-trimethyl-7-oxabicyclo[2.2.1]heptane of the formula VI

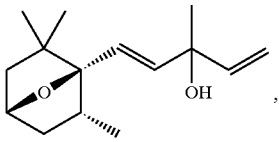

(VI)

and to a process for its preparation, which comprises the novel (4R,6R)-1-(3-oxo-1-butenyl)-2,2,6-trimethyl-7-oxabicyclo[2.2.1]heptane of the formula V

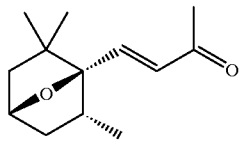

(V)

being, in a conventional way, vinylated or initially ethynylated and subsequently partially hydrogenated.

The invention also relates to a process for preparing a mixture of the $C_{15}$-triarylphosphonium salt of the formula III and the novel isomer of the formula iso-III

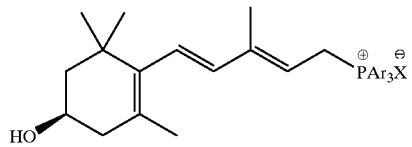

(III)

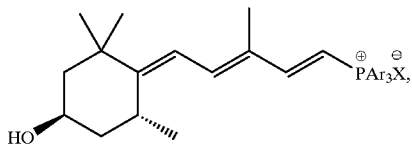

(iso-III)

where Ar is an aryl radical, preferably an unsubstituted or substituted phenyl radical, and X is one equivalent of an anion of a strong acid, in particular Cl, Br or (HSO$_4$), which comprises the novel (4R,6R)-1-(3-hydroxy-3-methyl-1,4-pentadienyl)-2,2,6-trimethyl-7-oxabicyclo[2.2.1]heptane of the formula VI,

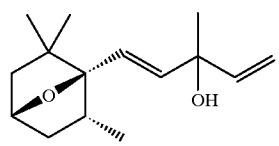

(VI)

being reacted with a triarylphosphine and a strong acid, and to the novel intermediates [5-(4R,6R)-(4-hydroxy-2,2,6-trimethyl-1-cyclohexylidene)-3-methyl-1,3-pentadienyl] triarylphosphonium salts of the formula iso-III

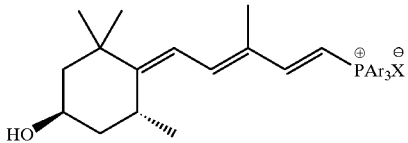

(iso-III)

mixed with the corresponding [5-(4R)-(4-hydroxy-2,2,6-trimethyl-1-cyclohexenyl)-3-methyl-2,4-pentadienyl] triarylphosphonium salts of the formula III

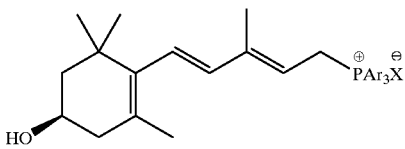

(III)

where Ar is an aryl radical, preferably an unsubstituted or substituted phenyl radical, and X is one equivalent of the anion of a strong acid.

Concerning step A:

The optically active (4R)-4-hydroxy-2,2,6-trimethylcyclohexanone of the formula II used as starting compound is a known compound for which a satisfactory industrial preparation is available (cf. Helv. Chim. Acta 73 (1990), 861).

The reaction of ketones with dichloromethyllithium is disclosed in the literature (cf. Tetrahedron Letters 27 (1973) 2465) and generally results in lithium dichloromethyl-carbinolates which, on heating, rearrange to a-chloro aldehydes with elimination of lithium chloride.

In the case of the (4R)-4-hydroxy-2,2,6-trimethylcyclohexanone of the formula II, the reaction with dichloromethyllithium surprisingly results in the novel $C_{10}$-aldehyde (4R,6R)-1-formyl-2,2,6-trimethyl-7-oxabicyclo [2.2.1]heptane of the formula IV.

The dichloromethyllithium required for this reaction step is prepared under the usual conditions, specifically by metallation of dichloromethane with alkyllithium compounds, in particular with the commercially available n-butyllithium, at from −120 to −70° C., preferably −90 to −60° C., or else with a lithium dialkylamide such as lithium diisopropylamide or lithium dicyclohexylamide, in particular a commercially available lithium diisopropylamide, at from −70 to −40° C., preferably −70 to −30° C. Conversion of the cyclohexanone of the formula II into the bicyclic aldehyde of the formula IV generally takes place by slow addition of this ketone at the abovementioned temperatures to the preparation solution of dichloromethyllithium and subsequent slow warming to from 20 to 60° C. The reaction mixture is advantageously warmed in the presence of catalytic amounts of an alkali metal alcoholate such as potassium tert-butoxide or sodium methoxide powder or of an alkali metal hydroxide such as LiOH, NaOH, KOH, preferably the low-cost NaOH. The reaction mixture is generally worked up by adding water and extracting with a solvent which is immiscible or only slightly miscible with water, such as suitable hydrocarbons, especially cyclohexane and hexane, or with an ether such as diethyl ether or methyl tert-butyl ether.

The yield for this conversion is about 85% of theory.

If it is wished to prepare zeaxanthin from the bicyclic aldehyde of the formula IV, it is possible to dispense with isolation of the aldehyde, without a deterioration in yield, ie. the aldehyde can be immediately reacted further in the form of the reaction mixture obtained in this step.

Concerning step B:

Conversion of the novel bicyclic $C_{10}$-aldehyde of the formula IV into the novel bicyclic $C_{13}$-ketone of the formula V with acetone can in principle take place by known methods, for example by a base-catalyzed condensation with acetone. Acetone is advantageously used in excess as solvent in this condensation. Examples of suitable basic catalysts are alkali metal hydroxides and alkaline earth metal hydroxides, especially alkali metal hydroxides. In a preferred embodiment of this condensation with acetone, the bicyclic aldehyde of the formula IV or the reaction mixture containing this aldehyde is mixed with about 10 to 20 times the molar amount of acetone and, after addition of an approximately equimolar amount of NaOH powder, the solution is refluxed for about 1 hour.

Another conventional possibility for converting the $C_{10}$-aldehyde of the formula IV into the $C_{13}$-ketone of the formula V is to react the $C_{10}$-aldehyde with diethyl 2-oxopropylphosphonate. Suitable bases in this case are, in particular, alkali metal alcoholates of lower alkanols, such as sodium methoxide. The reaction mixture is generally worked up in a conventional way, for example by removing solids from the reaction mixture by filtration, substantially evaporating the filtrate, taking the residue up in a nonpolar organic solvent, washing this solution with water, concentrating the organic phase, and purifying the novel ketone of the formula V by distillation.

Concerning step C:

The novel $C_{13}$-ketone of the formula V can also be converted into the novel $C_{15}$-carbinol of the formula VI by methods which are known in principle. It is possible, for example, firstly for the ketone to be converted by 1,2-addition of lithium or sodium acetylide into the novel (4R,6R)-1-(3-hydroxy-3-methyl-1-penten-4-ynyl)-2,2,6-trimethyl-7-oxabicyclo[2.2.1]heptane, and subsequently for the latter to undergo partial hydrogenation to the novel $C_{15}$-carbinol of the formula VI. The partial hydrogenation can then be carried out under the conditions known as Lindlar hydrogenation. For further details of the ethynylation of ketones and the partial hydrogenation of the resulting alkynes, we refer, for example, to W. Oroshnik et al., J. Chem. Soc. 1952, 74 and 295 and H. Lindlar, Helv. Chim. Acta 35 (1952), 35 and 445.

However, the novel $C_{13}$-ketone of the formula V can also be converted directly, in only one step, by 1,2-addition of vinyllithium or vinylmagnesium chloride into the novel $C_{15}$-carbinol of the formula VI. Preferred solvents for both reactions with organometallic compounds are liquid ammonia and tetrahydrofuran. For further details of the vinylation of ketones, we refer, for example, to Y. Ishikawa et al., Bull. Chem. Soc. Japan 37 (1964) 207.

The reaction mixture is generally worked up in a conventional way. It is possible, for example, to evaporate the reaction mixture, to treat the residue with water and a suitable nonpolar organic solvent, to concentrate the organic phase which has been separated off, and to purify the resulting crude product if necessary by distillation.

Concerning step D:

Conversion of the novel $C_{15}$-carbinol of the formula VI into the mixture of $C_{15}$-triarylphosphonium salt of the formula III and the novel isomeric $C_{15}$-triarylphosphonium salt of the formula iso-III also takes place by known methods. For example, the $C_{15}$-carbinol can be reacted with the appropriate triarylphosphine salt in an organic solvent at from $-10$ to $+40°$ C. Solvents advantageously used in this case are aprotic solvents such as dichloromethane or dimethylformamide. For further details of the reaction, we refer to M. Rosenberger et al., J. Org. Chem. 47 (1982) 47 and 2130. The triarylphosphine salts preferably used are triphenylphosphine hydrohalides or triphenylphosphine bisulfate, in particular triphenylphosphine hydrobromide or hydrochloride.

The $C_{15}$-triarylphosphonium salts III and iso-III are formed in a molar ratio which differs according to the configuration of the $C_{15}$-carbinol of the formula VI and depends on the reaction conditions. They can either be reacted further directly in the form of the resulting reaction mixture or else be isolated. For isolation, for example, the solvent is distilled off with simultaneous addition of ethyl acetoacetate or of toluene, and the mixture of triarylphosphonium salts III and iso-III which results in crystalline form is filtered off with suction.

Concerning step E:

Reaction of the $C_{15}$-triarylphosphonium salts of the formula III with the $C_{10}$-dialdehyde 2,7-dimethyl-2,4,6-octatrienedial of the formula VIII is disclosed in the literature (cf., for example, Helv. Chim. Acta 63 (1980) 1456–1462, especially 1460–61 and loc. cit. 73 (1990) 864). It takes place particularly well in aprotic solvents such as dichloromethane using organolithium compounds as mentioned in stage A, or else using 1,2-epoxybutane in ethanol under reflux.

The novel isomeric $C_{15}$-triarylphosphonium salts of the formula iso-III form the identical product in this reaction: (3R, 3'R)-zeaxanthin.

It is possible with the aid of the novel process to prepare zeaxanthin, which is in demand as nature-identical dye, in good yields from the readily available (4R)-4-hydroxy-2,2,6-trimethylcyclohexanone of the formula II substantially avoiding the prior art disadvantages in only 5 stages which can be carried out relatively well even industrially, via interesting novel intermediates.

Experimental part

EXAMPLE 1

(4R,6R)-1-Formyl-2,2,6-trimethyl-7-oxabicyclo[2.2.1] heptane (IV)

a) Reaction: 284 ml of a solution of n-butyllithium (0.45 mol) in hexane were added in about 30 minutes (min) to a solution of 45 ml (0.54 mol) of dichloromethane in 250 ml of a mixture of tetrahydrofuran (THF) and diethyl ether (4/1) at $-70°$ C., and stirred at $-70°$ C. for a further 30 min. 22.8 g (0.15 mol) of (4R)-4-hydroxy-2,2,6-trimethylcyclohexanone in 40 ml of a mixture of THF and diethyl ether (4/1) were added dropwise to this solution at $-70°$ C., and the mixture was then allowed to reach room temperature (RT) in about 2 hours (h). Then 2.7 g (0.05 mol) of sodium methoxide powder were added, and the mixture was slowly warmed to $50°$ C. until evolution of gas ceased.

b) Workup: The reaction mixture obtained as in Example 1a was mixed with 200 ml of water at RT, the upper phase was separated off, and the aqueous phase was extracted three times with 150 ml of hexane each time. The organic phases were combined, washed twice with 150 ml of water and evaporated (rotary evaporator). The residue of 25.5 g was distilled to result in 22.1 g of 1-formyl-2,2,6-trimethyl-7-oxabicyclo[2.2.1]heptane with a boiling point of 54–61° C. under 1.5 mbar, which is 90% pure according to gas chromatography (GC), (equivalent to a yield of 85% of theory). A byproduct was ascertained to be 1-hydroxymethyl-2,2,6-trimethyl-7-oxabicyclo[2.2.1]heptane (about 4% of theory). The structure of the product was evident for example from the $^1$H-NMR spectrum: 250 MHz, ($C_6D_6$), δ=1.09 (d, J=8 Hz, 3 H), 4.16 (t, J=6 Hz, 1 H), 9.94 (s, 1 H); $[α]_D^{25}$=−20.7 (c=1, ethanol).

EXAMPLE 2

Preparation of (4R,6R)-1-(3-oxo-1-butenyl)-2,2,6-trimethyl-7-oxabicyclo[2.2.1]heptane (V)

a) Reaction: 284 ml of a solution of n-butyllithium (0.45 mol) in hexane were added in about 30 min to a solution of 45 ml of dichloromethane in 250 ml of a mixture of THF and diethyl ether (4/1) at −70° C., and stirred at −70° C. for a further 30 min. 22.8 g (0.15 mol) of (4R)-4-hydroxy-2,2,6-trimethylcyclohexanone in 40 ml of THF/diethyl ether (4/1) were added dropwise to this solution at −70° C., and the mixture was then allowed to reach RT over the course of 2 h. Then 2.7 g of sodium methoxide powder were added, and the mixture was slowly warmed to 50° C. until evolution of gas ceased. The reaction mixture was then mixed with 250 ml of acetone and 8.5 g (0.2 mol) of NaOH powder and subsequently refluxed (about 57° C.) for 20 min.

b) Workup: The mixture was poured into 600 ml of water (W), and the organic phase was separated off and washed twice with 150 ml of W each time. The combined aqueous phases were extracted twice with 150 ml of hexane each time. The organic phases were combined and concentrated in a rotary evaporator to result in 37.2 g of residue. Distillation of this residue under reduced pressure in a 10 cm indented column afforded 27.9 g of 1-(3-oxo-1-butenyl)-2,2,6-trimethyl-7-oxabicyclo[2.2.1]heptane with a boiling point of 90–96° C. under 1 mbar, which was about 95% pure according to GC (equivalent to a yield of 85% of theory). The structure of the novel product was evident from examination by $^1$H-NMR and IR spectroscopy; 250 MHz ($C_6D_6$); δ=1.83 (s, 3H, CO—$CH_3$), 4.20 (t, 1H, OCH), 6.50 and 7.00 (d,d J=20 Hz, CH=CH); υ=1672 $cm^{-1}$ (C=O), 1630 $cm^{-1}$ (CH=CH); $[α]_D^{25}$=−20,7 (c=1, ethanol).

EXAMPLE 3

Preparation of (4R,6R)-1-(3-hydroxy-3-methyl-1,4-pentadienyl)-2,2,6-trimethyl-7-oxabicyclo[2.2.1]heptane (VI)

a) Reaction: A solution of 15.6 g (70 mmol) of the distilled ketone prepared in Example 2 in 20 ml of THF was added dropwise in 30 min to 80 ml of a 1.3 molar solution of vinylmagnesium chloride (about 100 mmol) in THF while cooling with an ice bath. The temperature was kept at 18–22° C. during this.

b) Workup: The reaction mixture obtained in a) was stirred for a further 30 min and then, while cooling with an ice/salt bath, 180 ml of 25% strength aqueous sodium hydroxide solution and 200 ml of methyl t-butyl ether (MTB) were added. The organic phase was separated off, the aqueous phase was washed twice with 100 ml of MTB each time, and the combined MTB phases were evaporated in a rotary evaporator to result in 22 g of 1-(3-hydroxy-3-methyl-1,4-pentadienyl)-2,2,6-trimethyl-7-oxabicyclo[2.2.1]heptane (GC determination of content: 90% area). Distillation of the resulting product under reduced pressure in a 10 cm indented column afforded 18.9 g of the abovementioned product with a boiling point of 94 to 99° C. under 1 mbar, which was 92% pure according to GC, equivalent to a yield of 95% of theory. The structure was assigned to the novel compound by means of $^1$H-NMR spectroscopy: 250 MHz (DMSO), δ=0.75; 0,95, 1.11 (3s, 3$CH_3$), 2.25 (m—H—$C_6$), 4.26 (t,H—$C_4$), 4.72 (s,OH), 4.88–5.94 (5-Vinyl-H). $[α]_D^{25}$=−27.5 (c=0.5, methanol)

EXAMPLE 4

Preparation of [5-(4R)-(4-hydroxy-2,2,6-trimethyl-1-cyclohexenyl)-3-methyl-2,4-pentadienyl] triphenylphosphonium bromide (IIIa) and [5-(4R,6R)-(4-hydroxy-2,2,6-trimethylcyclohexylidene)-3-methyl-1,3-pentadienyl]triphenylphosphonium bromide (iso-IIIa)

A solution of 2.47 g (10 mmol) of (4R, 6R)-1-(3-hydroxy-3-methyl-1,4-pentadienyl)-2,2,6-trimethyl-7-oxabicyclo [2.2.1]heptane (content 95%) in 5 ml of dichloromethane was added dropwise to a solution of 3.43 g (10 mmol) of triphenylphosphine hydrobromide and 0.13 g (0.5 mmol) of triphenylphosphine in 30 ml of dichloromethane while cooling in an ice bath. Stirring was then continued for 1 h while warming to RT.

The resulting reaction solution was then introduced dropwise over the course of 1 h in 600 ml of diethyl. After 2 h, the crystals which had formed were filtered off with suction, washed with 50 ml of diethyl ether and dried under a stream of nitrogen. 5.6 g, equivalent to 100% of theory, of a mixture of the abovementioned isomeric $C_{15}$-triphenylphosphonium bromides were obtained in roughly identical proportions. The structure was assigned on the basis of the $^1$H-NMR spectroscopic data:

250 MHz, (DCCl$_3$):

Compound IIIa δ=1,33 (d, $CH_3$), 1.60 (S, $CH_3$), 386–4.02 (m, HCO), 4.80–5.00 (m, $CH_2$-P), 5.24–5.39 (m, H—$C_2$) 5.90 (s, H—$C_4$ and H—$C_5$); Compound iso-IIIa δ=2.19 (s, $CH_3$), 3.19–3.26 (m, HCO), 6.32 and 6.56 (2d, J=20 Hz, H—$C_{4,5}$), 6.78 and 6.88 (2d, J=10 Hz, H—$C_{2,3}$).

EXAMPLE 5

Preparation of (3R, 3'R)-zeaxanthin (I)

The following reaction and workup were carried out with exclusion of moisture and atmospheric oxygen.

a) Reaction: 7.5 ml of a 1.6 molar solution (total 12 mmol) of n-butyllithium in hexane were added dropwise to a solution of 1.2 g (12 mmol) of diisopropylamine in 50 ml of diethyl ether at −10° C. The mixture was then stirred at −10° C. for 1 h. 5.6 g (10 mmol) of a 1:1 mixture of the triphenylphosphonium bromides III and iso-III obtained as in Example 4 were suspended in 50 ml of diethyl ether at −10° C. The solution of lithium diisopropylamide in diethyl ether obtained as described above was introduced dropwise into this suspension at −10° C., and the mixture was then stirred at −10° C. for 1 h. A solution of 0.57 g (3.5 mmol) of 2,6-dimethyl-2,4,6-octatrienedial (VIII) in 20 ml of dichloromethane was introduced dropwise into the resulting deep red solution of $C_{15}$ ylide at −10° C., and the mixture was then refluxed for 2 h.

b) Workup: The reaction mixture obtained in Example 5a was cooled to −10° C., and 70 ml of methanol were added dropwise. The crystals which had separated out were then filtered off and the filter cake was washed with 30 ml of methanol and dried under a stream of nitrogen to result in 1.8 g of (3R, 3'R)-zeaxanthin, equivalent to a yield of 90% of theory based on dialdehyde VII. According to HPLC analysis, the all-E isomer predominates in the resulting zeaxanthin.

The resulting zeaxanthin was purified and converted into (all-E) zeaxanthin by thermal isomerization and crystallization from dichloromethane/ethanol. The yield of pure (all-E) zeaxanthin was 1.6 g, equivalent to 81% of theory based on dialdehyde VIII.

We claim:

1. A process for preparing (3R,3'R)-zeaxanthin of the formula I

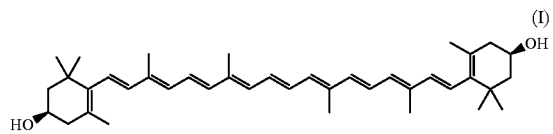

(I)

which comprises

A. (4R)-4-hydroxy-2,2,6-trimethylcyclohexanone of the formula II

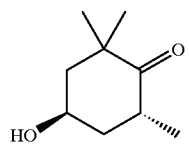

(II)

being reacted with dichloromethyl lithium in an inert solvent at from −120 to −40° C., B. the novel (4R,6R)-1-formyl-2,2,6-trimethyl-7-oxabicyclo[2.2.1]heptane of the formula IV

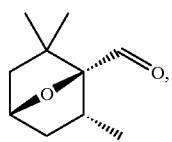

(IV)

which is obtained on warming the reaction mixture to 20 to 60° C., being reacted either in isolated form, or else directly in the form of the resulting reaction mixture with acetone or a dialkyl 2-oxopropylphosphonate, C. the resulting novel (4R,6R)-1-(3-oxo-1-butenyl)-2,2,6-trimethyl-7-oxabicyclo[2.2.1]heptane of the formula V

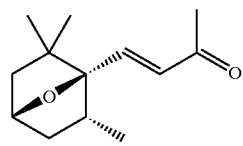

(V)

being converted by vinylation or ethynylation and subsequent partial hydrogenation into the novel (4R,6R)-1-(3-hydroxy-3-methyl-1,4-pentadienyl)-2,2,6-trimethyl-7-oxabicyclo[2.2.1]heptane of the formula VI

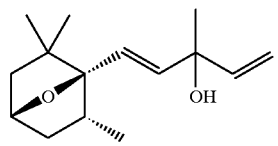

(VI)

D. the latter being reacted with a triarylphosphine, and a strong acid to give a mixture of the $C_{15}$-triarylphosphonium salt of the formula III and the novel isomer of the formula iso-III

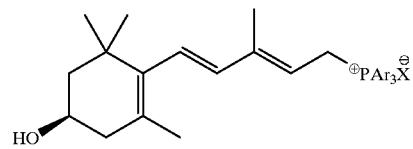

(III)

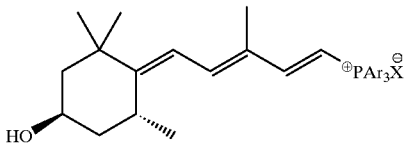

(iso-III)

where Ar is an aryl radical, and X is one equivalent of an anion of a strong acid, and E. in each case about 2 mol of the resulting mixture of the $C_{15}$-triarylphosphonium salt III and the novel iso-III being converted by a double Wittig reaction with 2,7-dimethyl-2,4,6-octatrienedial of the formula VIII

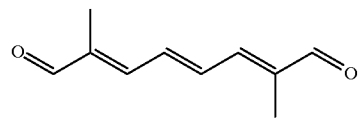

(VIII)

into zeaxanthin of the formula I.

2. A process for preparing the novel (4R,6R)-1-formyl-2,2,6-trimethyl-7-oxabicyclo[2.2.1]heptane of the formula IV

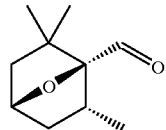

(IV)

which comprises (4R)-4-hydroxy-2,2,6-trimethylcylohexanone of the formula II (II)

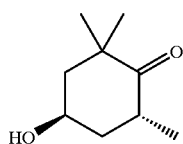

being reacted with dichloromethyllithium in an inert solvent at from −120 to −40° C., and the resulting reaction mixture being formed, in the presence or absence of an alkali metal alcoholate or an alkali metal hydroxide, at a temperature from 20 to 60° C.

3. (4R,6R)-1-Formyl-2,2,6-trimethyl-7-oxabicyclo[2.2.1]heptane of the formula IV (IV)

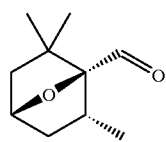

4. A process for preparing the novel (4R,6R)-1-(3-oxo-1-butenyl)-2,2,6-trimethyl-7-oxabicyclo[2.2.1]heptane of the formula V (V)

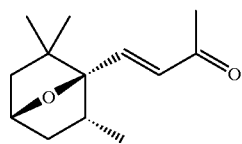

which comprises the novel (4R,6R)-1-formyl-2,2,6-trimethyl-7-oxabicyclo[2.2.1]heptane of the formula IV (IV)

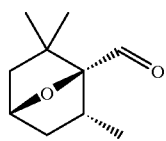

being reacted either in isolated form or directly in the form of the reaction mixture obtained on reacting (4R)-4-hydroxy-2,2,6-trimethylcyclohexanone of the formula II (II)

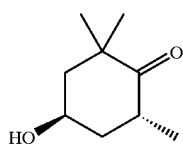

with dichloromethyllithium, which has been obtained by metallation of dichloromethane with alkyllithium compounds at from −120 to −70° C. or with lithium dialkylamides at from −70° C. to −40° C., in an inert solvent at from −120 to −40° C., and subsequently warming to 20 to 60° C., with acetone in an aldol condensation.

5. (4R,6R)-1-(3-Oxo-1-butenyl)-2,2,6-trimethyl-7-oxabicyclo[2.2.1]heptane of the formula V (V)

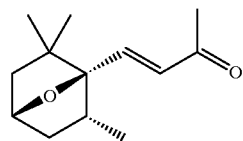

6. A process for preparing the novel (4R,6R)-1-(3-hydroxy-3-methyl-1,4-pentadienyl)-2,2,6-trimethyl-7-oxabicyclo[2.2.1]heptane of the formula VI (VI)

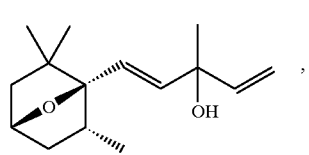

which comprises the novel (4R,6R)-1-(3-oxo-1-butenyl)-2,2,6-trimethyl-7-oxabicyclo[2.2.1]heptane of the formula V (V)

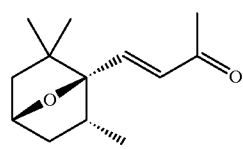

being, vinylated or initially ethynylated and subsequently partially hydrogenated.

7. A process for preparing a mixture of the $C_{15}$-triarylphosphonium salt of the formula III and the novel isomer of the formula iso-III (III)

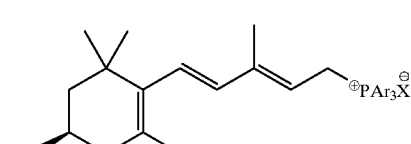

(iso-III)

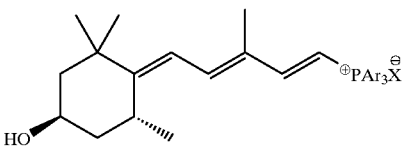

where Ar is an aryl radical, and

X is one equivalent of an anion of a strong acid, which comprises the novel (4R,6R)-1-(3-hydroxy-3-methyl-1,4-pentadienyl)-2,2,6-trimethyl-7-oxabicyclo[2.2.1] heptane of the formula VI

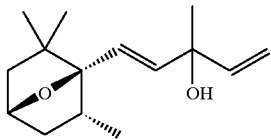

(VI)

being reacted with a triarylphosphine and a strong acid.

8. [5-(4R,6R)-(4-hydroxy-2,2,6-trimethyl-1-cyclohexylidene)-3-methyl-1,3-pentadienyl]triarylphosphonium salt of the formula iso-III

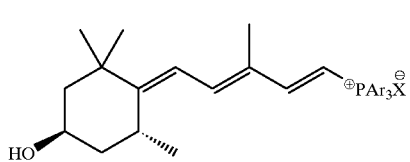

(iso-III)

mixed with the corresponding [5-(4R)-(4-hydroxy-2,2,6-trimethyl-1-cyclohexenyl)-3-methyl-2,4-pentadienyl]triarylphosphonium salt of the formula III

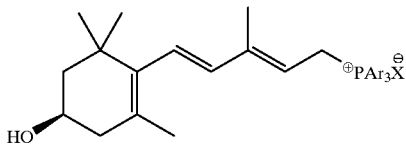

(III)

where Ar is an aryl radical, and X is one equivalent of the anion of a strong acid.

9. A process for preparing (3R, 3'R)-zeaxanthin, which comprises a novel [5-(4R,6R)-(4-hydroxy-2,2,6-trimethyl-1-cyclohexylidene)-3-methyl-1,3-pentadienyl] triarylphosphonium salt of the formula iso-III or a mixture of this novel triarylphosphonium salt of the formula iso-III and a [5-(4R)-(4-hydroxy-2,2,6-trimethyl-1-cyclohexenyl)-3-methyl-2,4-pentadienyl]triarylphosphonium salt of the formula III being reacted in a double Wittig reaction with 2,7-dimethyl-2,4,6-octatrienedial.

10. A process as claimed in claim 2, wherein the dichloromethyllithium required for reaction stage A is prepared by metallation of dichloromethane with butyllithium at a temperature of −90 to −60° C. or with a lithium dialkylamide at a temperature of −70 to −30° C.

11. A process according to claim 1 where Ar is a substituted or unsubstituted phenyl radical and X is Cl, Br or $HSO_4$.

12. A process according to claim 7 wherein Ar is a substituted or unsubstituted phenyl radical and X is Cl, Br or $HSO_4$.

13. A salt according to claim 8 where Ar is a substituted or unsubstituted phenyl radical and X is Cl, Br or $HSO_4$.

* * * * *